Figure 1:
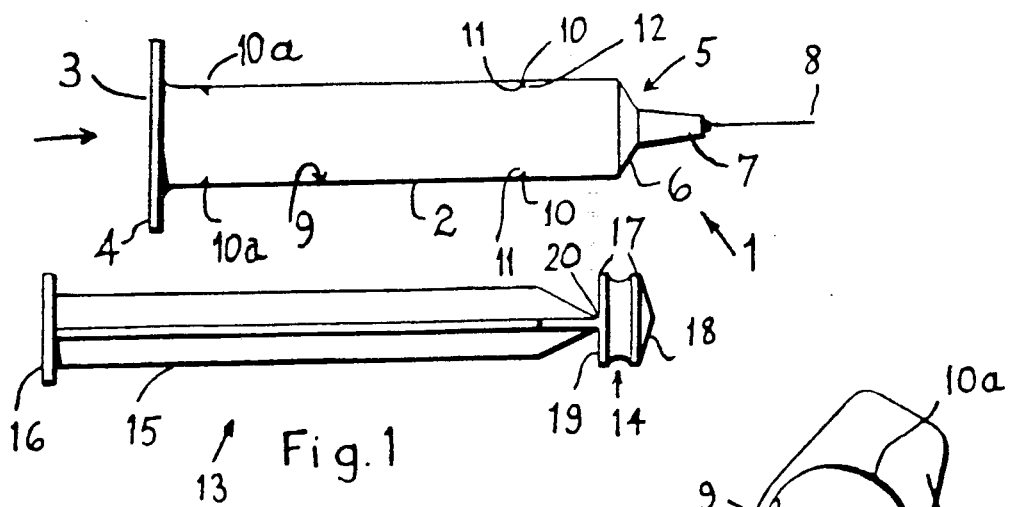

United States Patent [19]

Koska

[11] Patent Number: 5,047,017

[45] Date of Patent: Sep. 10, 1991

[54] SYRINGE

[75] Inventor: Marc Koska, Turnbridge Wells, United Kingdom

[73] Assignee: Agven Medical Corporation Limited, London, England

[21] Appl. No.: 438,456

[22] PCT Filed: Jun. 24, 1988

[86] PCT No.: PCT/GB88/00490

§ 371 Date: Dec. 21, 1989

§ 102(e) Date: Dec. 21, 1989

[87] PCT Pub. No.: WO88/10127

PCT Pub. Date: Dec. 29, 1988

[30] Foreign Application Priority Data

Jun. 25, 1987 [GB] United Kingdom ............... 8714923
Jan. 29, 1988 [GB] United Kingdom ............... 8801992

[51] Int. Cl.$^5$ ............................................. A61M 5/00
[52] U.S. Cl. ................................. 604/110; 604/218; 604/228
[58] Field of Search ............... 604/110, 218, 187, 220, 604/208, 210, 228

[56] References Cited

U.S. PATENT DOCUMENTS

| | | |
|---|---|---|
| 3,934,586 | 1/1976 | Easton et al. . |
| 3,951,146 | 4/1976 | Chiquiar-Arias . |
| 4,220,151 | 9/1980 | Whitney . |
| 4,233,975 | 11/1980 | Yerman . |
| 4,252,118 | 2/1981 | Richard et al. . |
| 4,270,536 | 6/1981 | Lemelson . |
| 4,367,738 | 1/1983 | Legendre et al. . |
| 4,710,170 | 12/1987 | Habel et al. . |
| 4,775,364 | 10/1988 | Alles ..................... 604/228 |

FOREIGN PATENT DOCUMENTS

| | | | |
|---|---|---|---|
| 523179 | 3/1956 | Canada ................. 604/220 |
| 112893 | 1/1969 | Denmark ............. 604/110 |
| 0339954 | of 0000 | European Pat. Off. . |
| 0229017A2 | 1/1987 | European Pat. Off. . |
| 1532874 | of 0000 | France . |
| 1567778 | 5/1969 | France . |
| 2348708 | 11/1977 | France . |
| WO89/08468 | of 0000 | PCT Int'l Appl. . |
| WO8802640 | 6/1988 | PCT Int'l Appl. . |
| 1550310 | 8/1979 | United Kingdom . |
| 2015883A | 9/1979 | United Kingdom . |
| 2117249A | 10/1983 | United Kingdom . |
| 2184657A | 1/1985 | United Kingdom . |

OTHER PUBLICATIONS

Third report from the Social Services Committee Session 1986-87 "Problems Associated with Aids", vol. I, May 13, 1987.
Turkish Search Report for Turkish Patent Application TR 31772/88.

Primary Examiner—John D. Yasko
Attorney, Agent, or Firm—Panitch Schwarze Jacobs & Nadel

[57] ABSTRACT

A single-use syringe which may be constructed for use by drug abusers comprises a barrel (2) and a plunger (13) slidably mounted in the barrel (2) with the plunger stopper (14) sealingly engaging with the inner wall of the barrel (2). Projections (10) extend from the inner wall of the barrel (2) and are located at such a distance from the distal end of the barrel (2) to permit flushing movements of the stopper (14). A breakable joint (20) integrally joins the stopper (14) and the plunger rod (15), and is broken by engagement of the stopper (14) with the projections (10), so that the stopper is retained in the end of the barrel and the syringe is rendered unfit for further use. In one embodiment, the joint is resilient such that the joint moves readily past the projections during full advance of the plunger to inject a drug, but engages the projections thereby breaking the joint, during subsequent withdrawal of the plunger.

20 Claims, 13 Drawing Sheets

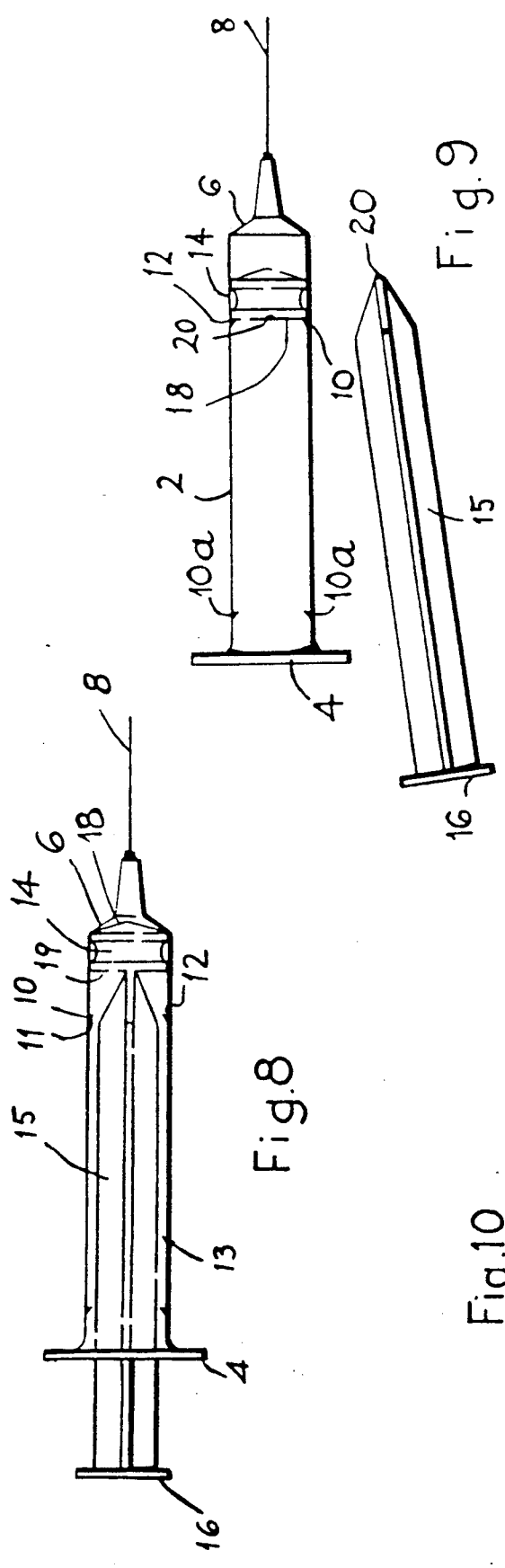
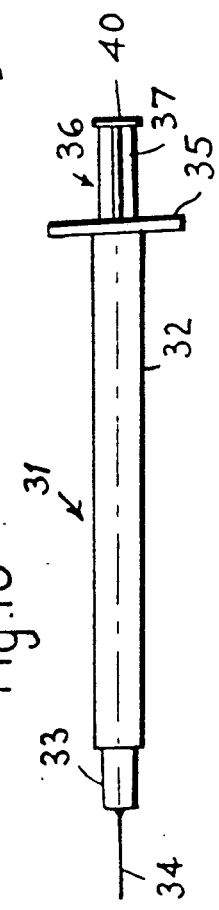
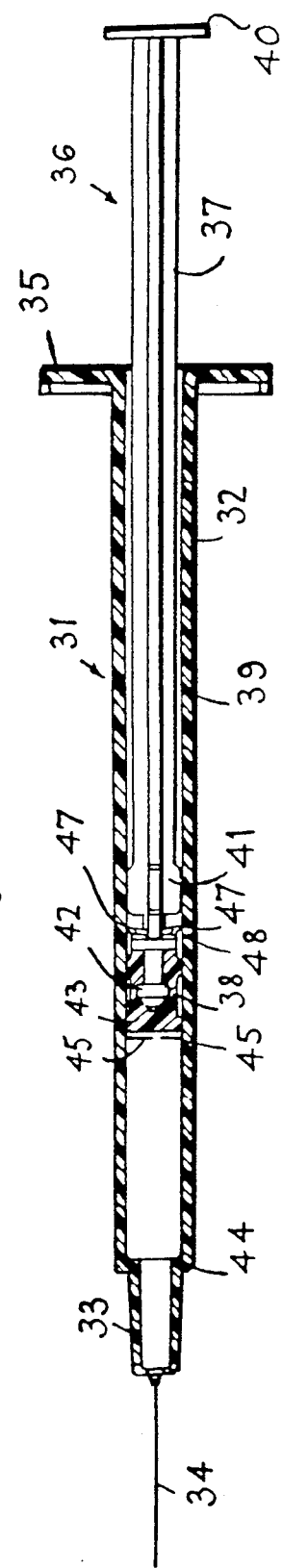

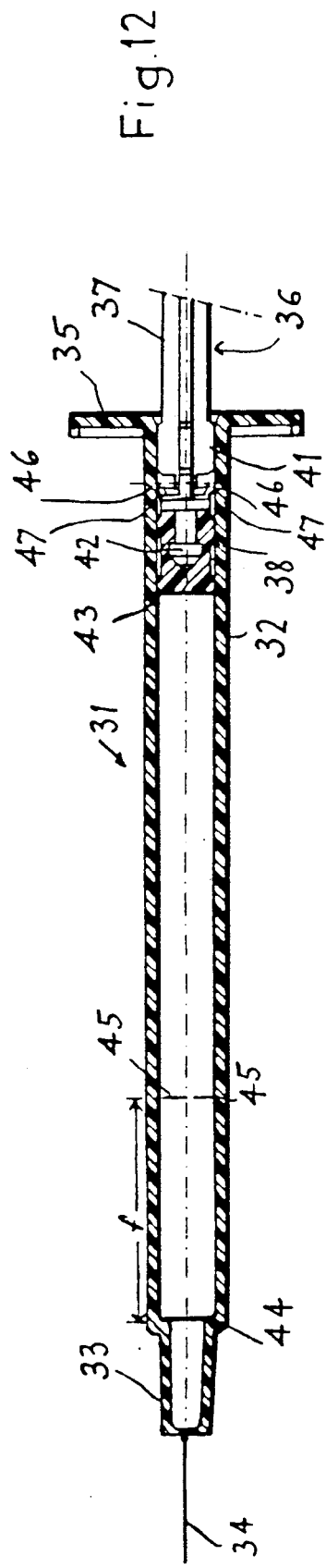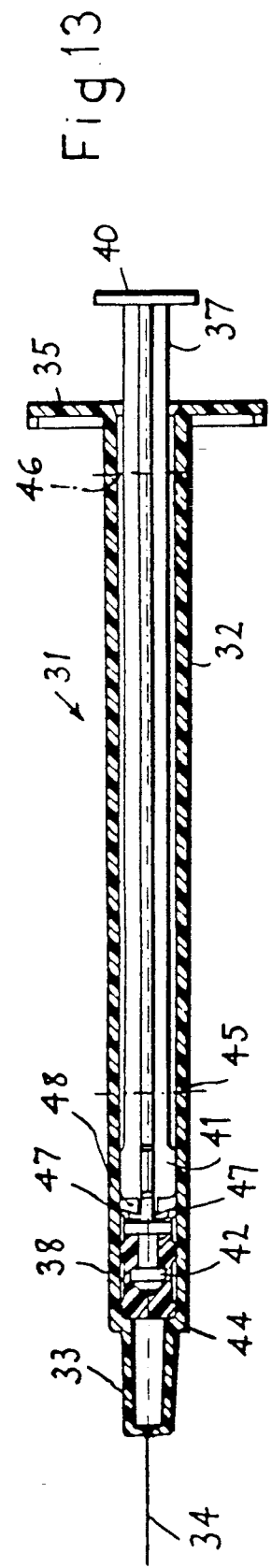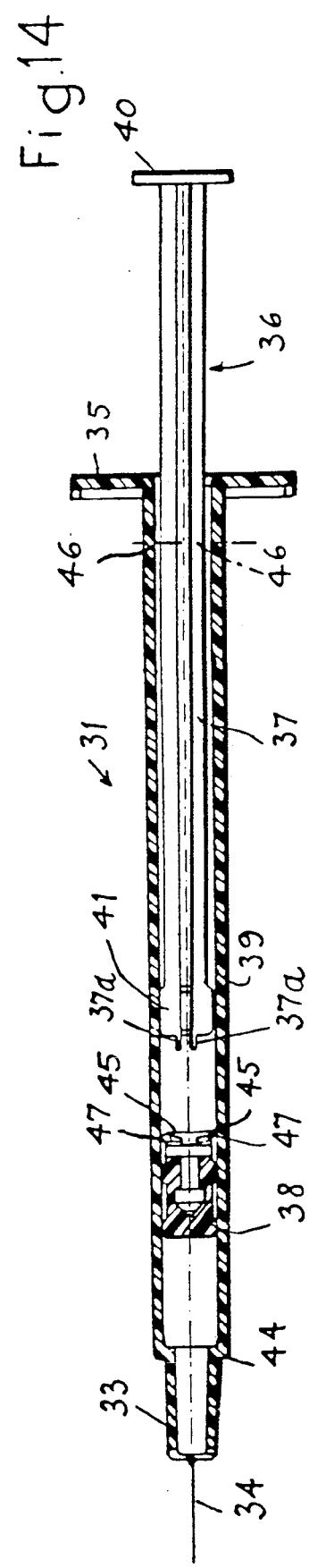

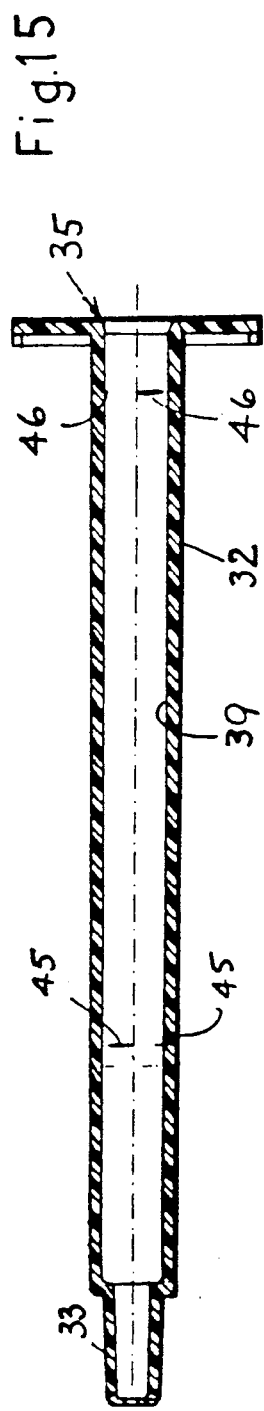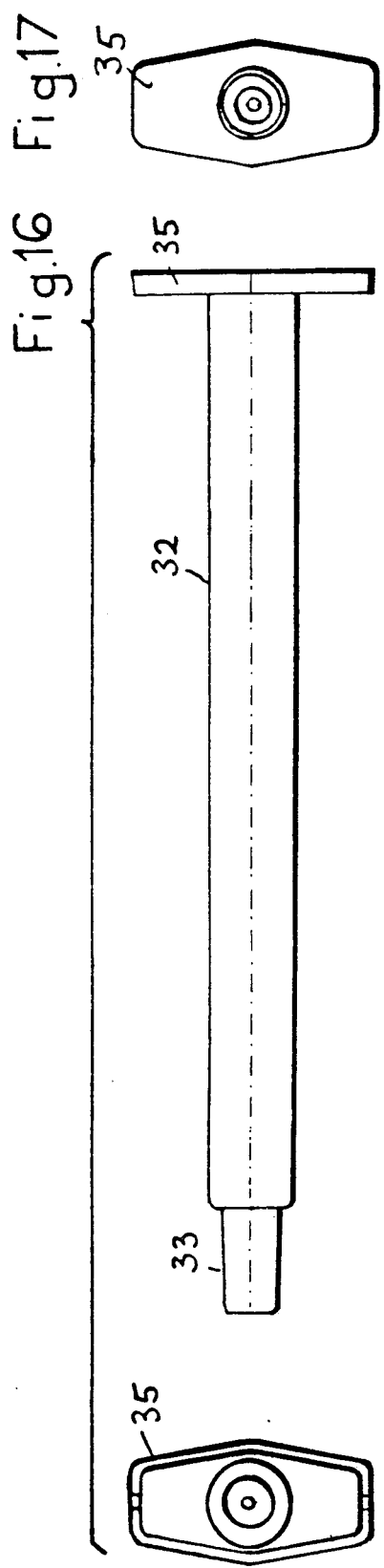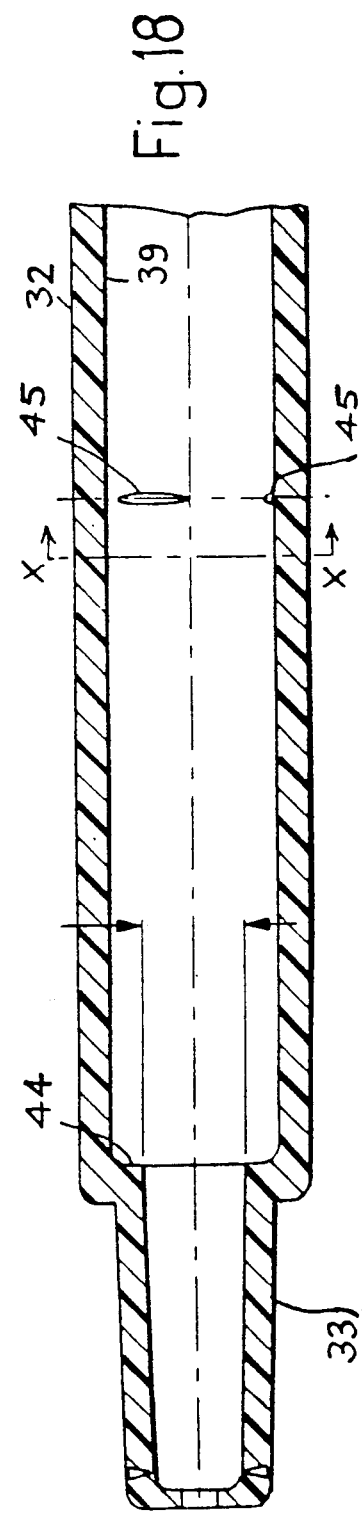

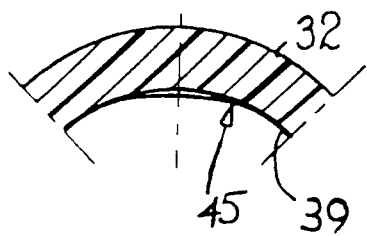
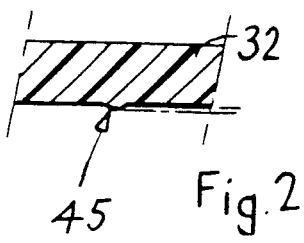
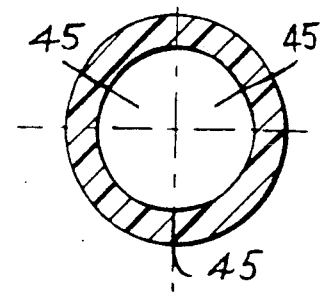
Fig.19  Fig.20  Fig.21
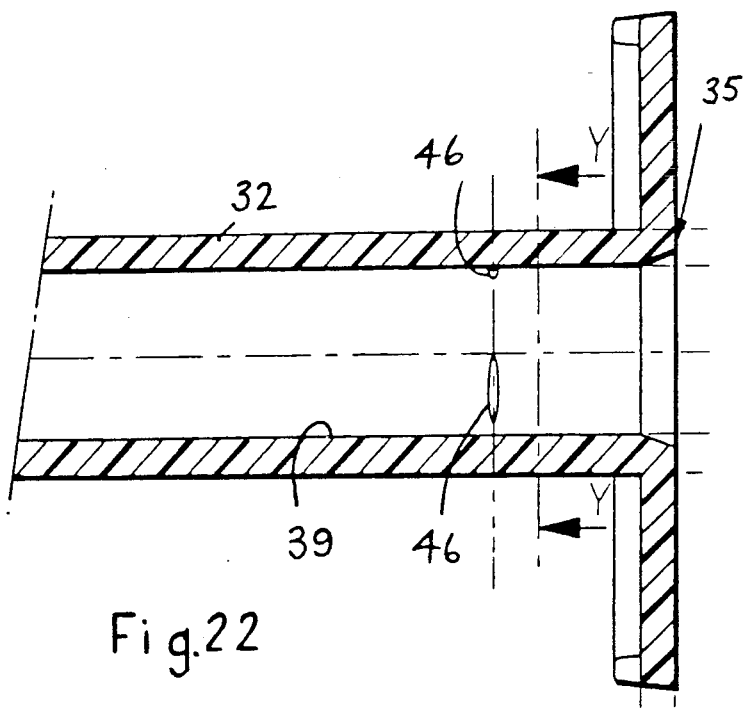
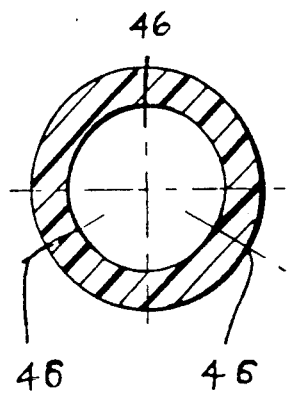
Fig.22  Fig.23
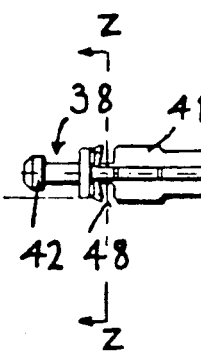
Fig.24
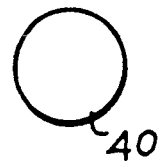
Fig.24a

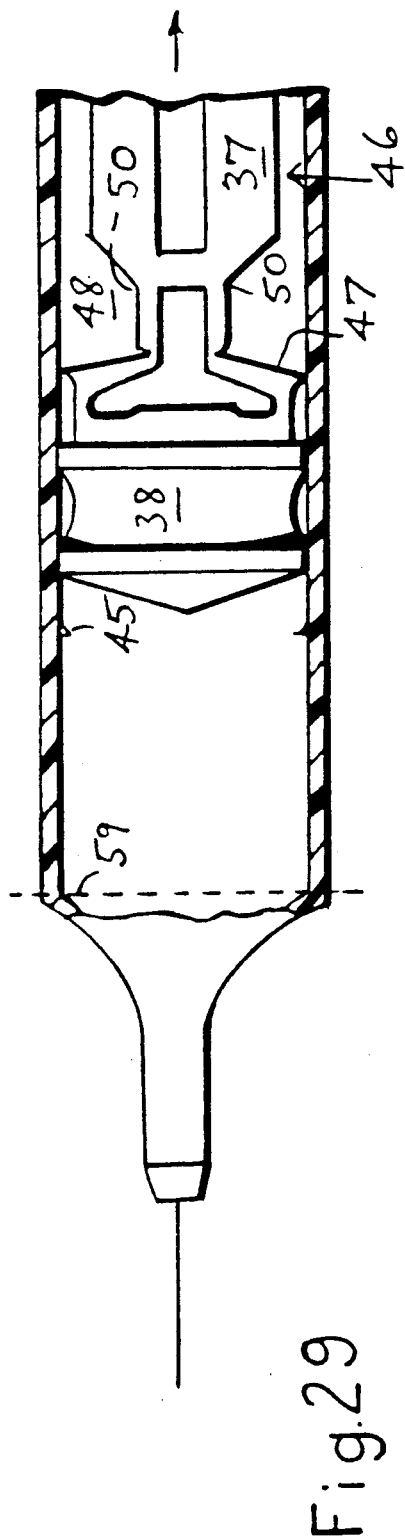
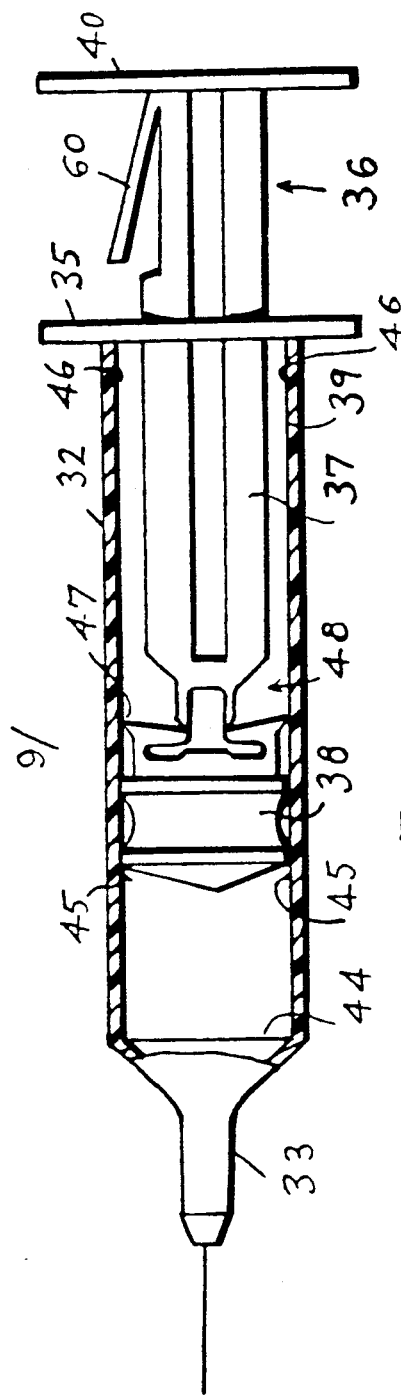
Fig.29
Fig.30

SYRINGE

This invention relates to syringes and has for its object a syringe which can only be used once.

In recent years, the greatest and most serious public health problem has been the threat of AIDS. It has been reported that about 50% of those people who are AIDS carriers or HIV positive are intravenous drug abusers and it is now of tantamount importance to prevent the spread of the AIDS virus not only among drug abusers but also from that group into the wider community.

A need has thus developed for a "safe" syringe which will render itself useless after one drug shot and which is tamperproof, with the purpose of eliminating shared use of syringes and thus reducing the spread of AIDS. This need has already been highlighted in the Third Report from the Social Services Committee, "Problems Associated with AIDS" volume 1, 13th May 1987.

To this end, many attempts have been made to provide such a single-use syringe, and these known syringes all tend to make use of one of the following techniques to try to prevent them being suitable for re-use:

(i) Puncturing or cutting of the syringe barrel during, or at the end of, advance of the syringe plunger to inject the drug, for example as shown in U.S. Pat. No. 3,951,146, (ii) Fracturing of the needle connector by the syringe user after a single use, for example as shown in U.S. Pat. No. 4,220,151, (iii) Using a multipart plunger, of which one part, usually the plunger stopper is detachable without breaking from another part, usually the plunger rod, during withdrawal after a single use, as shown for example in U.S. Pat. No. 4,252,118, (iv) Engagement of the plunger stopper behind a trapping member hinged to the syringe barrel upon full advance of the plunger, as in for example GB-A-2184657, (v) Locking of the plunger rod upon full withdrawal after use, as in for example U.S. Pat. No. 3,478,937, (vi) Use of a pre-filled syringe and a one-stroke plunger wherein only advance movement of the plunger is possible, for example in U.S. Pat. No. 4,367,738, (vii) Breaking, or at least deforming connections between the plunger stepper and plunger rod to the extent that it is no longer possible to retract the stopper for re-use, as in for example EP-A-0229017.

At present, however, none of these known single-use syringes meet the requirements of the drug abuser and none are in commercial production to the best of the applicant's knowledge. These known single-use syringes are generally either too costly or too complicated to manufacture and, in some instances, are totally impractical for drug abusers because they require a positive action by the user before the syringe is rendered useless and drug abusers cannot be relied upon to carry out this action.

Furthermore, it is necessary that the design of such a syringe takes into account all of the specific ritualistic habits of a drug addict during intravenous drug injection or otherwise use of the syringe will be unacceptable to these people. These habits include many insertions of the needle and small blood withdrawals to locate a suitable vein for injection which can be extremely difficult in long-term drug addicts. It is also vital that, after injection of the drug, the drug addict can flush with blood any drug remaining in the bottom part of the syringe barrel several times to ensure that all the drug is injected.

Schemes have now also been set up to provide a free source of clean syringes, together with counselling, for those who are at high risk from infection. Whilst such schemes are seen as being highly beneficial, they do require a syringe which guarantees that their objectives are met and, indeed, it is possible that without such a product, their work may be discontinued.

Whilst, drug abusers are a major problem in prevention of the spread of the AIDS virus, there are other obvious potential users who are to a greater or lesser extent also in need of a suitable "safe" syringe, particularly in the medical profession for general use in hospitals and by general practitioners. In the third world, these are many charities and government aid projects, which involve the purchase and supply of syringes to instigate health programmes in underdeveloped or disaster areas. In particular, the World Health Organisation requires a "safe" syringe for immunisation purposes in which specific quantities, usually as small as 0.5 ml, of vaccine can be accurately measured. Diabetics are also users of disposable syringes. Clearly, even in the best facility, a syringe may be used a second time in error or the method of disposal of used syringes may occasionally result in drug abusers obtaining dirty needles.

To the best of the Applicant's knowledge, there is no "safe" syringe commercially available on the market today which is cost-effective to manufacture, practical and compatible with all of the different requirements of syringe users.

It is therefore an object of the present invention to provide a syringe which can only be used once and which is tamper-proof, as well as being cheap and easy to manufacture, not relying on positive action by the user to render it useless, and functionable in such a way as to meet all the requirements of drug abusers, as well as of the medical profession in general.

Accordingly, the present invention consists in a syringe comprising a barrel and a plunger in slidable and sealing engagement with the inner wall of the barrel, the barrel having projection means and the plunger having breakable means, characterized in that the projection means project from the inner wall of the barrel and into the path of movement of the plunger stopper and in that the breakable means is integral with at least a part of the plunger rod and constitutes a breakable connection between said at least one part of the plunger rod and the plunger stopper, the arrangement being such that during either one of advance and withdrawl of the plunger engagement of the plunger with the projection means causes the breakable connection to break and thus the plunger stopper to break away from the said at least one part of the plunger rod.

By means of the present invention, the plunger rod becomes permanently detached from the plunger stopper, and the stopper is retained within the barrel by the projection means.

Advantageously, the plunger is arranged to engage with the projection means during withdrawal of the plunger following a full advance injection stroke and said projection means is located at such a distance from the distal end of the barrel to permit flushing movements of the plunger stopper prior to the breakable means being broken. In this way, the syringe is made particularly suitable for use by drug abusers, who need to ensure that all the drug is flushed out of the syringe.

The nature of the projection means may be such that the plunger stopper can easily slide over it during advance of the plunger to discharge a drug therefrom yet cannot move beyond the projection means during withdrawal so that any further withdrawal after the stopper has engaged with the projection means causes the stopper to break away from the plunger rod.

In one embodiment, to effect breakage between the plunger stopper and the plunger rod, an integral breakable junction is provided therebetween which is of reduced diameter or alternatively is made weaker than the plunger rod and stopper. Fracture or breakage of the junction occurs due to axial stress induced therein when the plunger stopper engages the projection means during withdrawal of the plunger after a maximum injection stroke.

In another embodiment of the invention, the breakable means is resilient and moves radially outward to engage with the inner wall of the barrel during the withdrawal stroke of the plunger and moves radially inwards to disengage the barrel inner wall during the advance stroke of the plunger such that the breakable means moves readily past the projection means during maximum advance of the plunger to inject a liquid from the syringe barrel but engages with the projection means during an attempt at a full withdrawal stroke following a maximum advance injection stroke, whereby to cause breakage of the resilient breakable means and permanent detachment of the plunger rod from the plunger stopper as the withdrawal stroke is continued.

By virtue of the resilient breakable means, once the projection means are engaged, further withdrawal of the plunger increases the engagement force, thereby greatly facilitating breakage of the plunger rod from the stopper which remains trapped in the distal end region of the barrel by the projection means.

Moreover, the resilient breakable means also enhances the tamper-proof characteristics of the syringe. For example, if after injection but before withdrawal and breakage, a drug abuser, in an attempt to reuse were to cut off the syringe barrel, push out the stopper, file down the outer periphery of the breakable means until it will no longer engage with the inner wall of the barrel when it is replaced, and glue back the distal end of the barrel, then the resilience of the breakable means will not allow the stopper to move during withdrawal but will break rendering the syringe unfit for use.

Furthermore, by virtue of this invention, the syringe has effectively two parts, which means a considerable reduction in moulding costs, one part being the barrel with the needle being moulded in and the other being the plunger. Although, the plunger itself may be, as is known be made with a peg over which an elastomeric cap is fitted to engage with the inner barrel wall, the plastics moulding of the plunger is still in one piece as if the whole plunger were made of the moulding plastics and engaged with the inner wall like the first embodiment described hereinabove.

Preferably, in order to prevent total withdrawal of the plunger from the barrel once the plunger has been inserted, another projection means is provided nearer the proximal end of the barrel.

Since there is always a possibility of the plunger being accidentally or inadvertently advanced so that the outer periphery of the breakable means is located distally of the distal projection means, for example during transport or packaging or removal from the packaging, advantageously, means are provided for preventing this occurring. In one embodiment such advance prevention means are located in the proximal end region of the plunger rod and in a normal position, causes interengagement between the plunger rod and syringe barrel to prevent such unwanted advance of the plunger in the barrel.

In a preferred embodiment, the advance prevention means consists in a sprung arm moulded integrally with the distal end region of the plunger rod which in its normal position engages with the distal end of the barrel but can be pushed in to allow the full advance stroke of the plunger to take place.

Preferably, the distal projection means comprises three distal projections which are of arcuate form and which are equispaced around the inner circumference of the barrel.

When there are a proximal projection means, this also preferably comprises three projections which are equispaced around the inner circumference of the barrel such that they occupy positions which are intermediate, and are equispaced from, the distal projections.

In another embodiment, the projection means comprises at least one ring extending around the circumference of the barrel inner wall.

In a preferred embodiment of the invention the outer periphery of the resilient breakable means comprises at least two wings, barbs, hooks, pointed projections or the like (hereinafter referred to generically as wings) which are engageable with and disengageable from respectively the inner wall of the barrel during the withdrawal stroke and advance stroke with the resilience being provided by the wings each being flexibly joined to the stopper at a radially outer location adjacent the barrel inner wall and at a radially inner location adjacent the plunger axis.

Furthermore, the syringe allows relatively free movement of the plunger in the syringe barrel to enable vein location to take place, while the syringe is being filled and during injection, but during withdrawal for further use the plunger stopper is broken or fractured from its integral connection with the plunger rod by engagement with at least one projection from the wall of the syringe barrel, leaving the stopper trapped behind the projection. By locating the projection a sufficient distance from the end of the syringe barrel, i.e. the position of maximum stroke or injection of the plunger, the syringe incorporates a short "flush-back" movement, which enables the drug abuser to flush with blood any drug remaining in the bottom part of the syringe barrel several times so that all the drug is injected, but yet does not allow the syringe to be reused for a further injection.

Also, the syringe in accordance with the invention is tamper-proof in that the joint between the fractured plunger parts is so small that it does not permit of gluing the parts together and even if the end of the syringe barrel were cut, it would be virtually impossible for the projections to be filled down sufficiently for the syringe to be usable as a syringe, after the end of the barrel had been stuck on again by the drug abuser. Of course, the syringe could be re-used either by making sure that the plunger stopper never passes the at least one projection which would entail the waste of an amount of drug solution that would be unacceptable to the drug abuser, or by using the small flush-back movement only which would make filling the syringe with an acceptable amount of drug and vein location impracticable.

In accordance with another embodiment of the invention, the plunger comprises two parts which are slidably interconnected to form a lost motion mechanism with the breakable means being integral with one of said parts and the outer part including the plunger stopper. The one part may be formed with two longitudinal grooves and the other part may be formed with hooks which are respectively slidably movable within the grooves. The projection means is preferably in annular form extending around the inner circumference of the barrel, for example in the form of a plurality of rings each located at respective predetermined distances from the distal end of the barrel. In this way, each ring can define a respective predetermined quantity of liquid to be injected, for example a 0.5 ml quality of vaccine, and the lost motion effect enables liquid to be drawn into the barrel to the level of the requisite ring without causing premature engagement, and thus breakage, of the breakable means.

Figure 2:
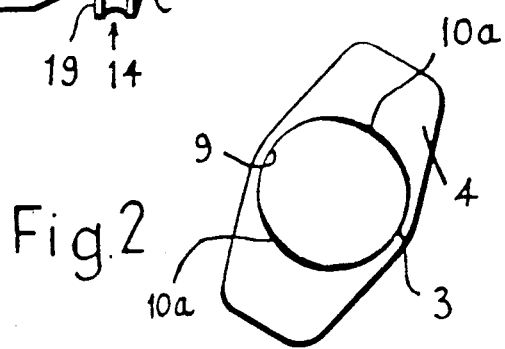
Figure 3:
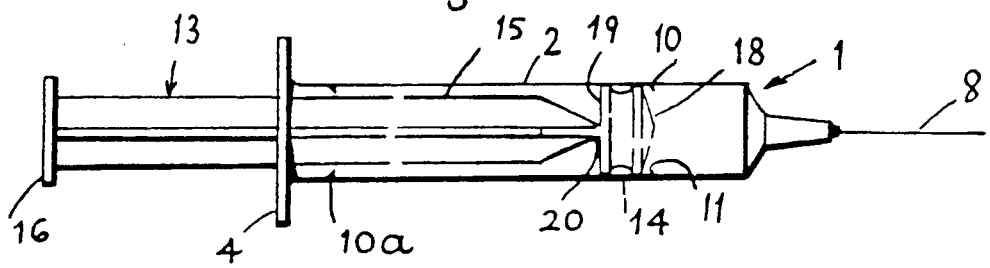
Figure 4:
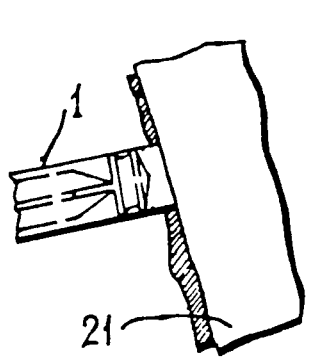
Figure 5:
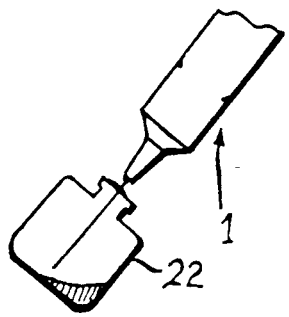
Figure 25:
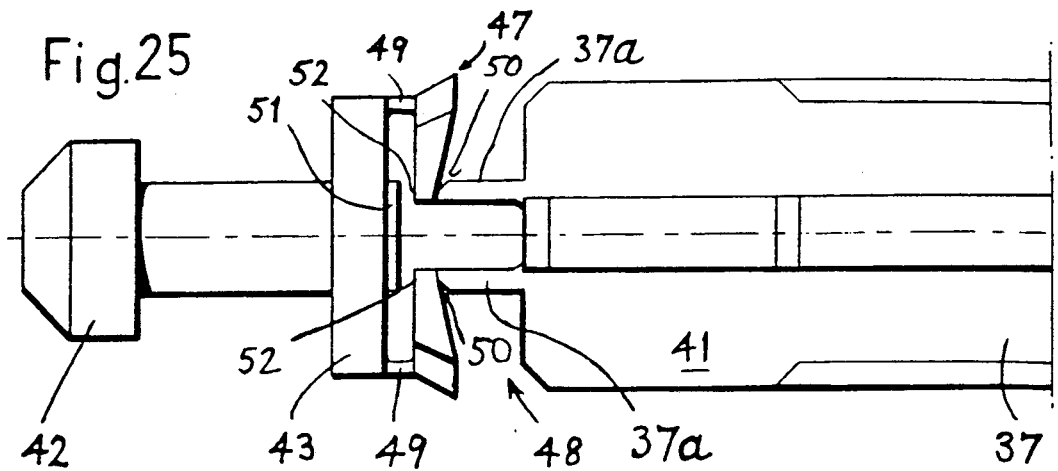
Figure 26:
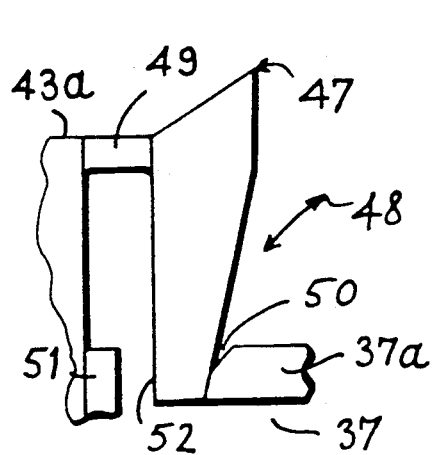
Figure 27:
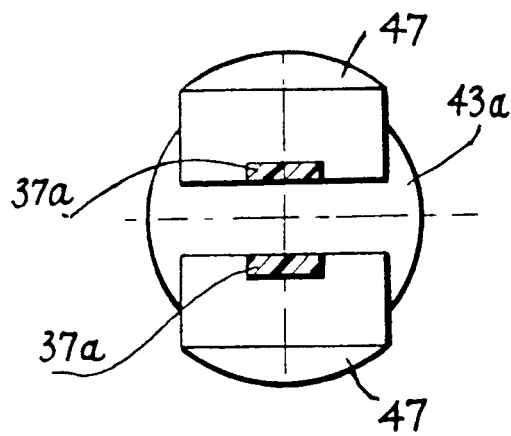
Figure 28A:
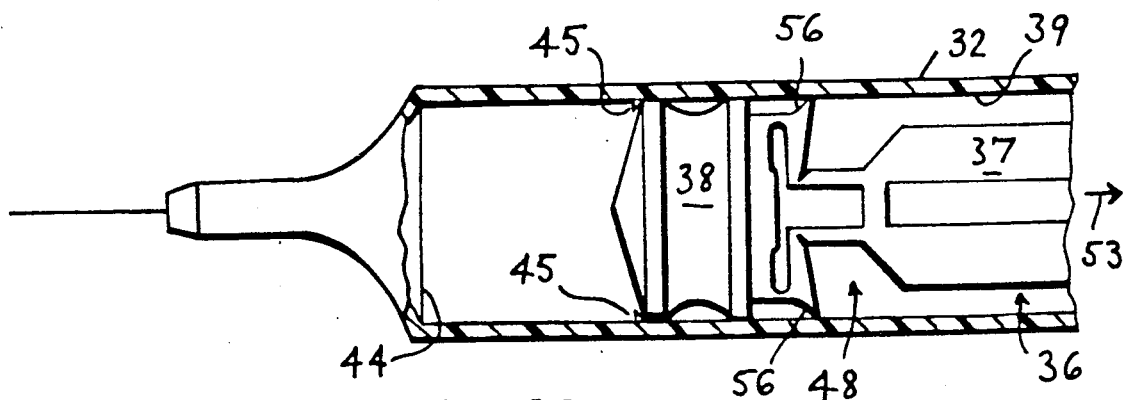
Figure 28B:
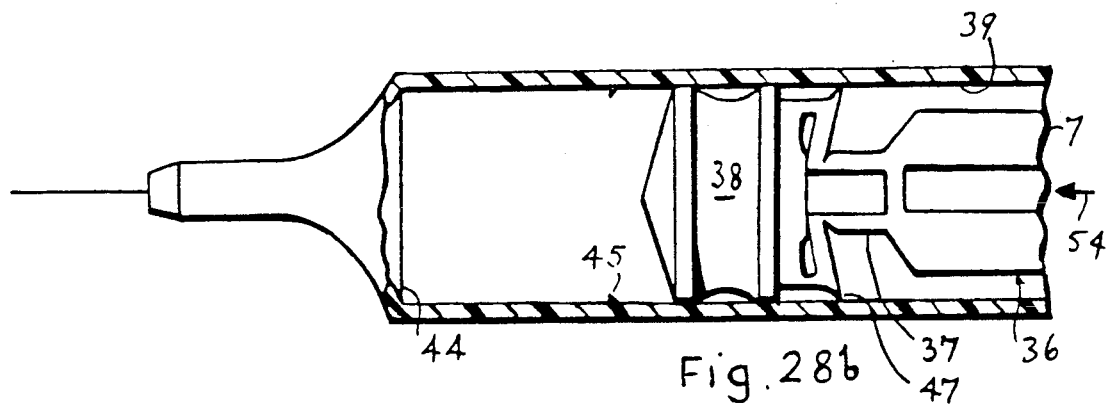
Figure 28C:
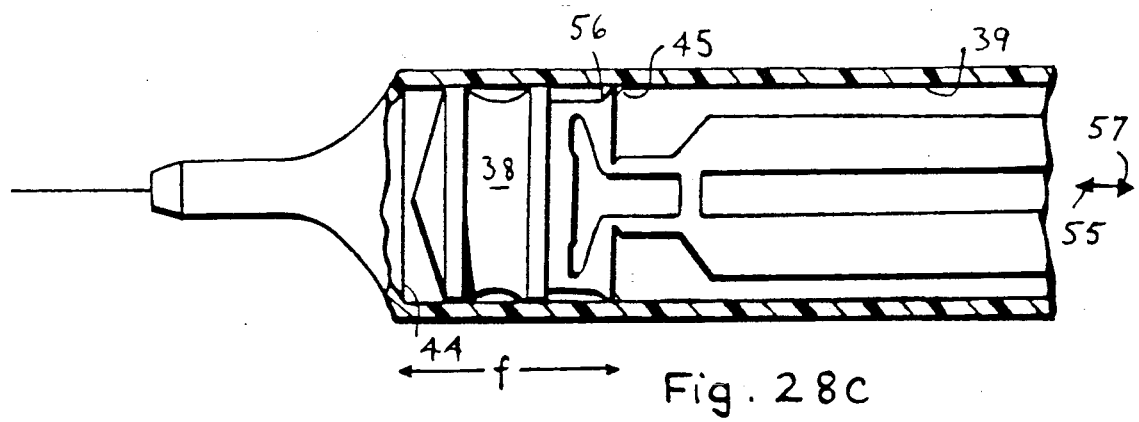
Figure 28D:
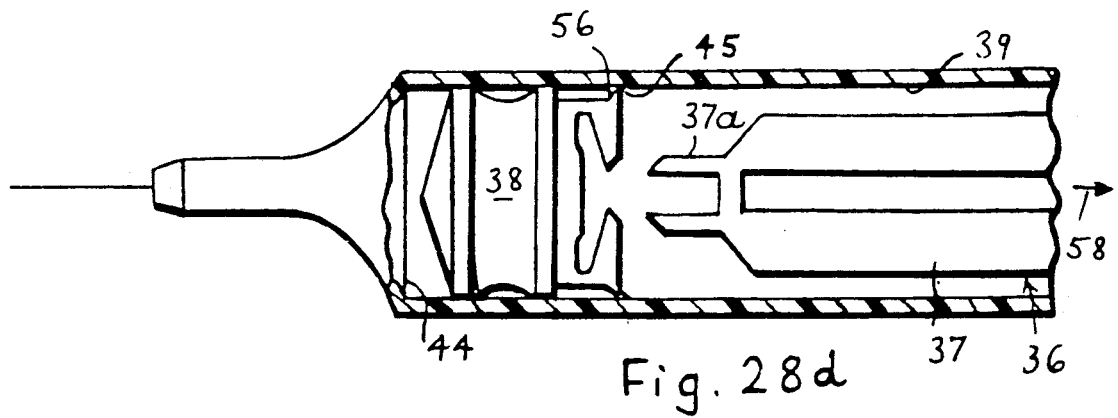
Figure 31:
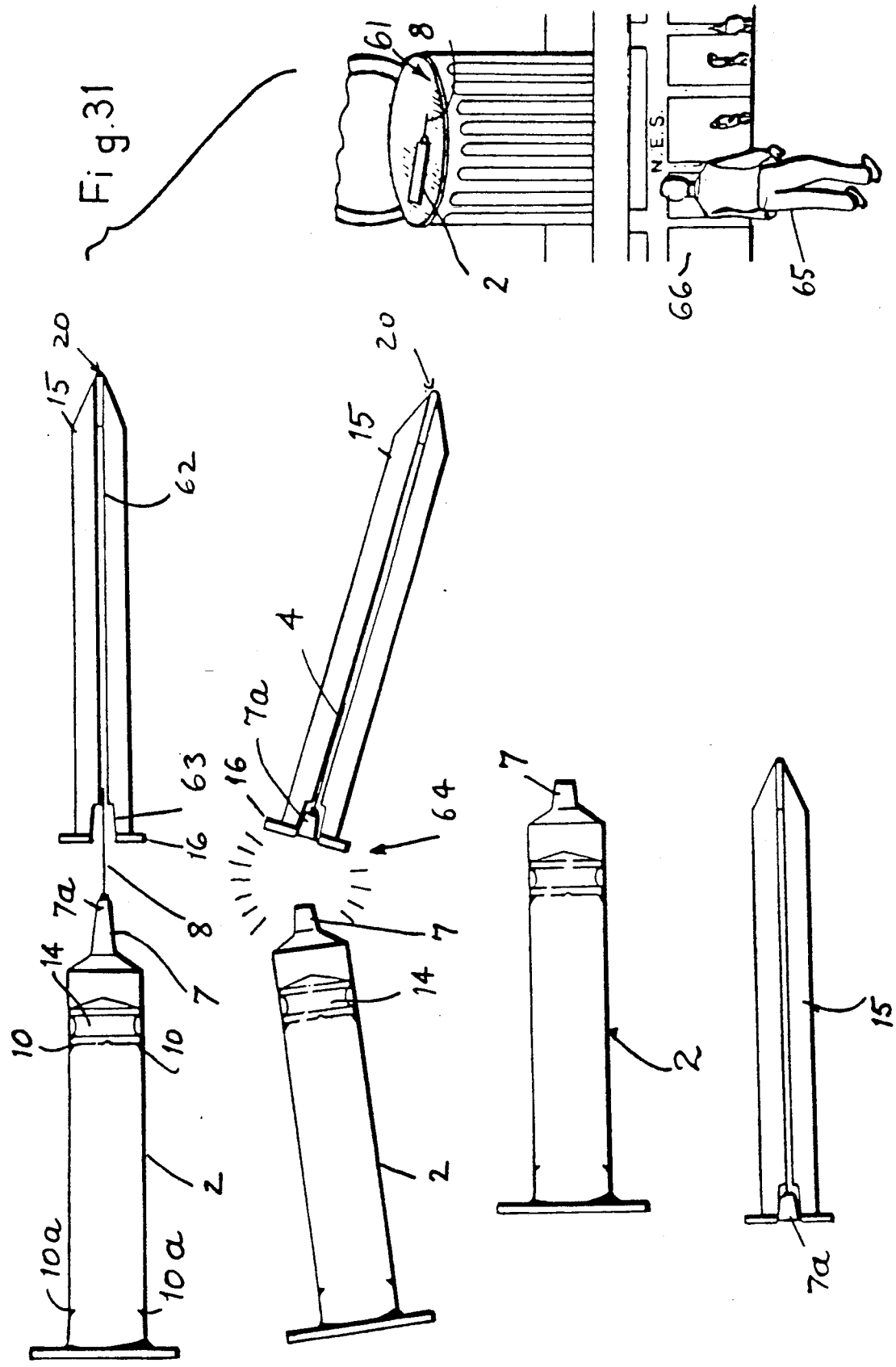

In order that the invention may be more readily understood, embodiments thereof will now be described by way of example, with reference to the accompanying drawings, in which:

FIG. 1 is a side elevation of a syringe constructed in accordance with one embodiment of the invention, showing the syringe prior to assembly with the syringe plunger outside the syringe barrel, FIG. 2 is an end view of the barrel of the syringe of FIG. 1 looking in the direction of the arrow, FIG. 3 is a side elevation of the syringe of FIG. 1 showing the syringe assembled with the plunger in the barrel and with the piston at a location ready for drawing liquid into the syringe barrel, FIGS. 4 to 9 show successive stages in the use of the syringe, FIG. 10 is an actual size side elevation of a one use only syringe constructed in accordance with another embodiment of the invention, FIGS. 11 to 13 are cross-sectional side elevations of the syringe of FIG. 10 showing the syringe plunger in different positions, FIG. 14 is a part-sectional side elevation of the syringe of FIG. 10 showing the plunger stopper broken from the plunger rod, FIGS. 15, 16 and 17 are a longitudinal section, a side elevation and an end view respectively of the syringe barrel of the syringe in FIG. 10, FIG. 18 is a longitudinal section of the distal end region of the syringe barrel, to an enlarged scale, FIGS. 19 and 20 are detail views of FIG. 18, FIG. 21 is a cross section taken along the lines X—X of FIG. 18 and looking in the direction of the illustrated arrows, FIG. 22 is a longitudinal section of the proximal end region of the syringe barrel, to an enlarged scale, FIG. 23 is a cross-section taken along the line Y—Y of FIG. 22 and looking in the direction of the illustrated arrows, FIG. 24 and 24a are a side elevation and an end view respectively of the plunger rod of the syringe, FIG. 25 is an enlarged view of the distal end region of the plunger stopper, FIG. 26 is a distal view, to a large scale of the plunger piston, FIG. 27 is an enlarged cross-section taken along the line Z—Z of FIG. 24 and looking in the direction of the illustrated arrows, FIGS. 28a to 28c are diagrammatic sketches of the distal end region of the syringe showing the distal end region of the syringe plunger in three different positions, FIG. 28d is a diagrammatic sketch of the distal end region of the syringe showing the plunger stopper broken from the plunger rod, FIG. 29 is a diagrammatic view of the distal end region of the syringe and showing tamper-proof characteristics of the syringe plunger, FIG. 30 is a diagrammatic side elevation of another embodiment, FIG. 31 illustrates one method of dis-enabling the syringe needle after its once only use to avoid contamination, e.g. by inadvertent pricking, by a bare needle, thrown away e.g. in the garbage.

Figure 32:
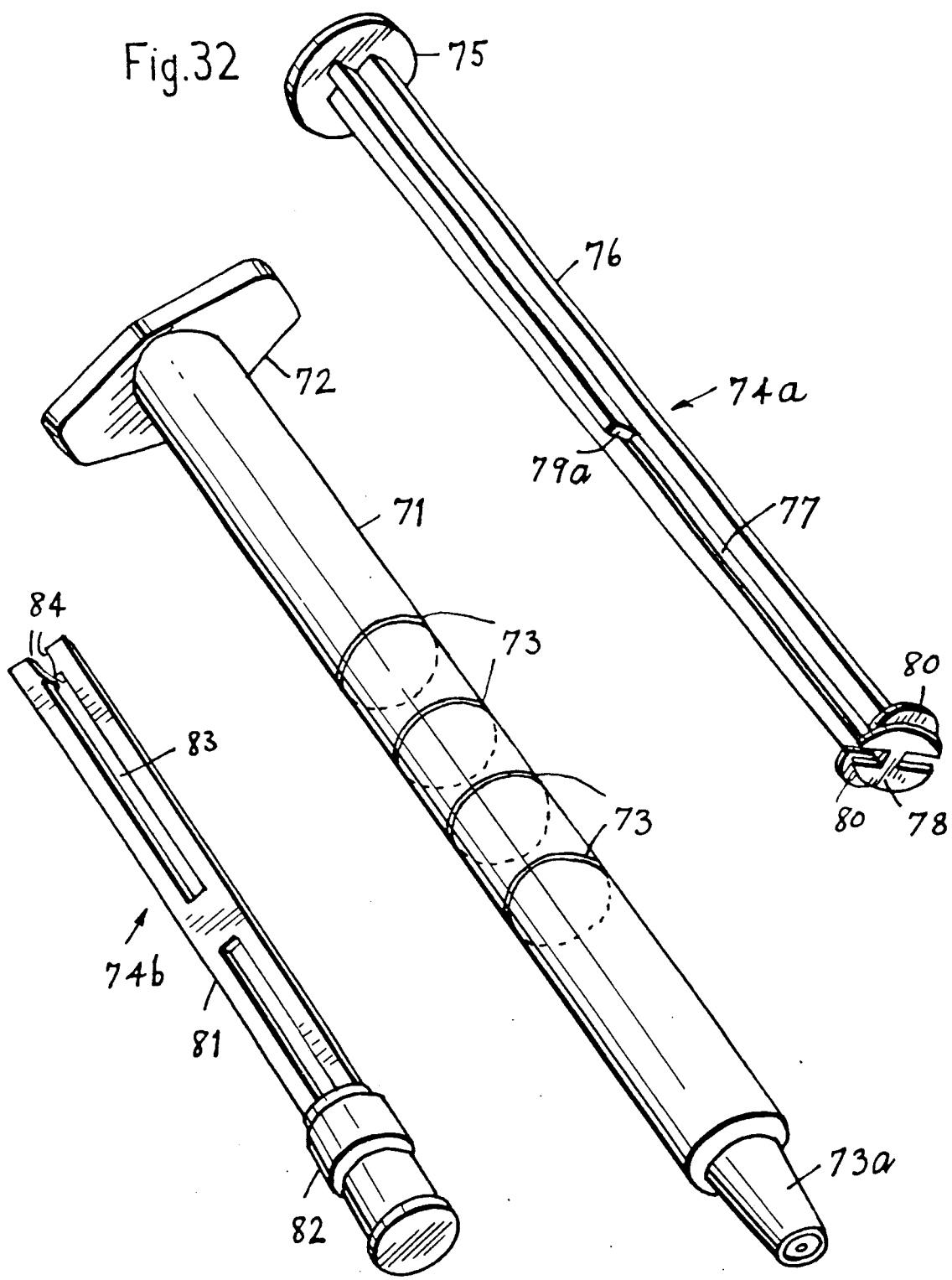
Figure 33:
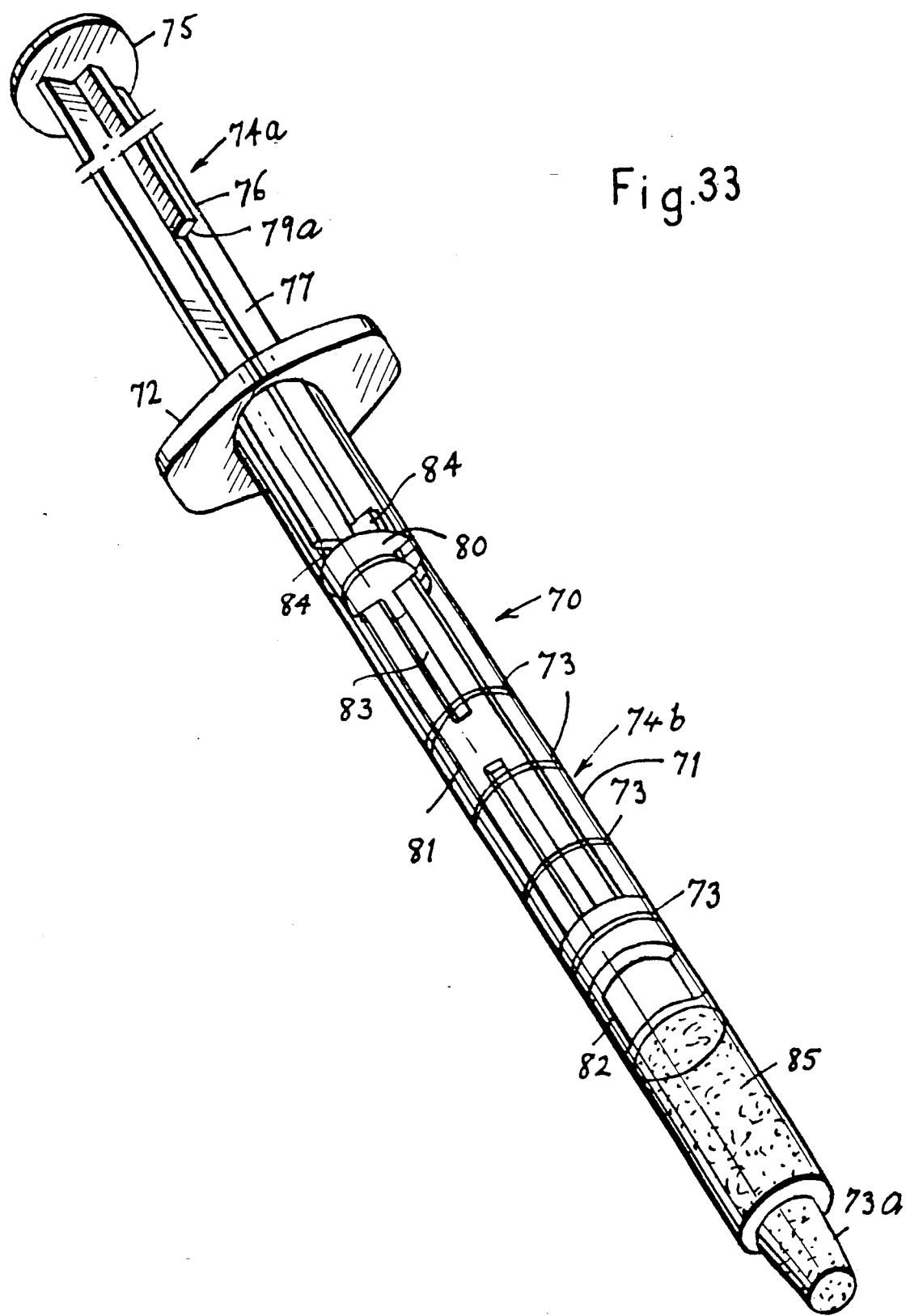
Figure 34:
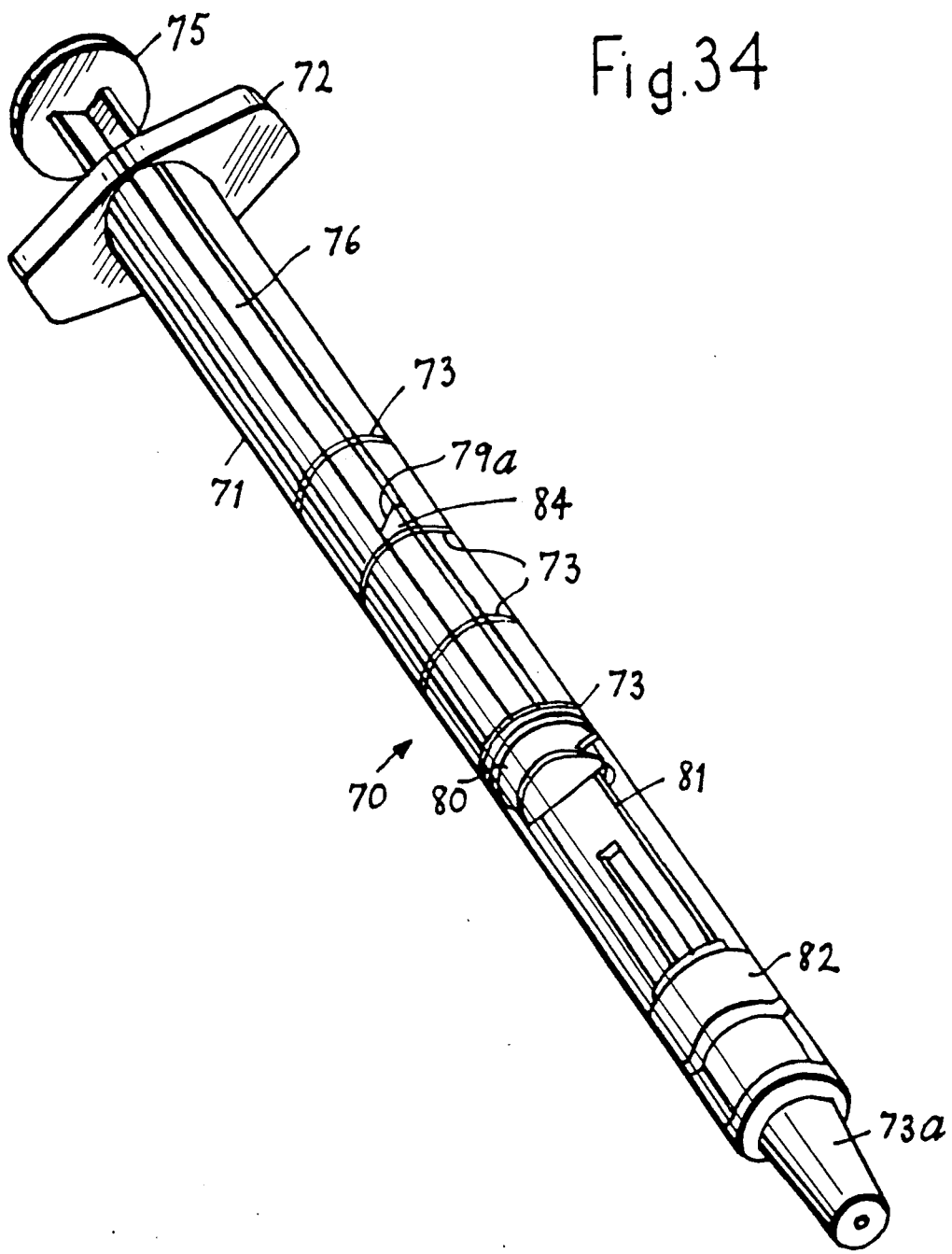
Figure 35:
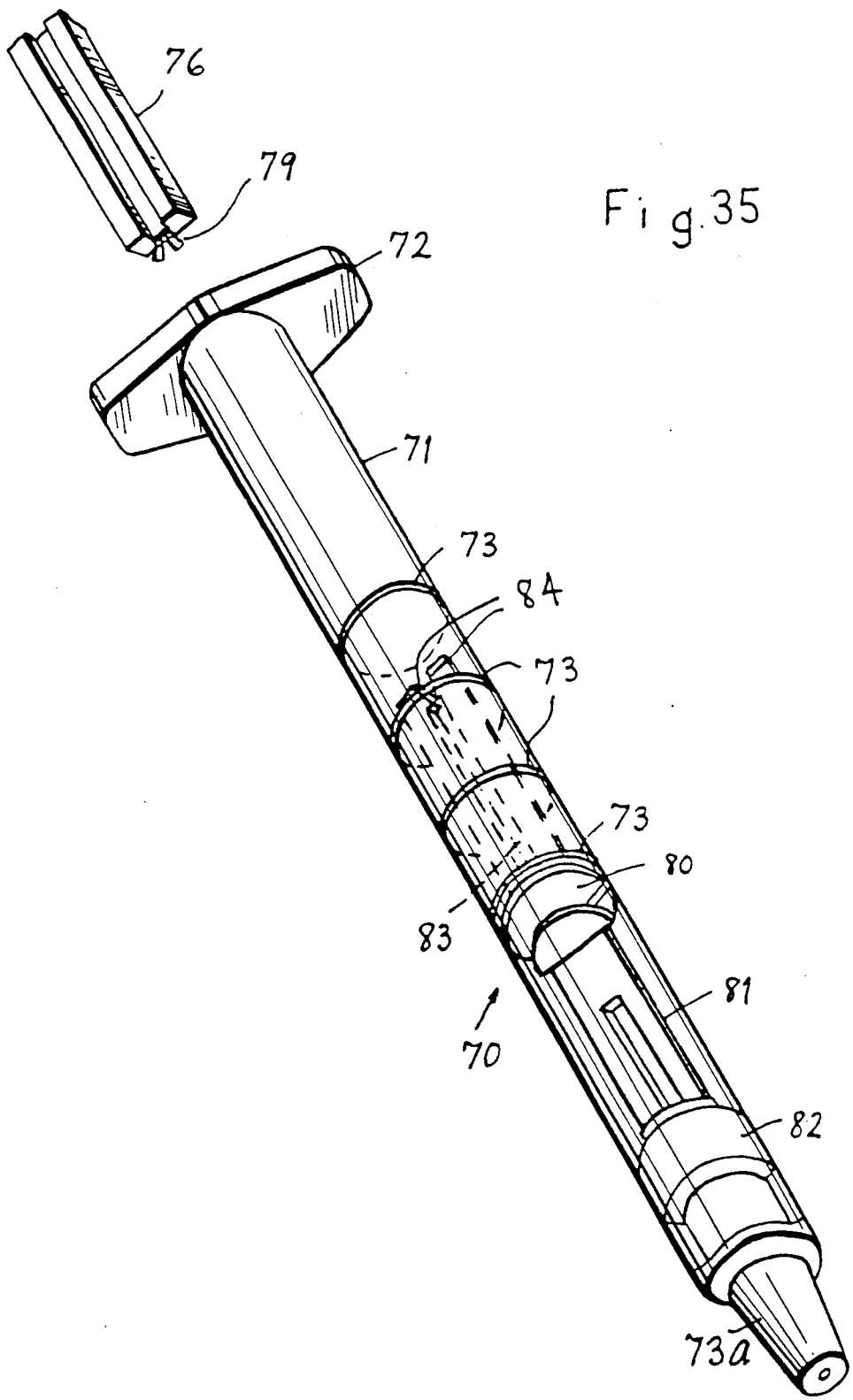

FIG. 32 is a perspective view of another embodiment of the present invention, showing the syringe prior to assembly with the syringe plunger outside the syringe barrel and FIGS. 33 to 35 illustrate successive stages in the use of the syringe shown in FIG. 32.

Referring to FIGS. 1 and 2 of the drawings the syringe, which is generally indicated by the reference 1, comprises a barrel 2 having an open proximal end 3 provided with a peripheral gripping member 4 and a distal end 5 having an internal abutment shoulder 6 encircling a liquid outlet and an integral mounting 7 for a needle 8 which is non-removably fixed thereto.

Nearer the distal end 5 of the barrel 2 the inner wall 9 of the barrel is provided with two diametrically opposed arcuate (crescent shaped) projections 10. The projections 10 each have a surface 11 which is inclined at an angle of less than 90°, e.g. 45°, to the inner wall 9 and which faces the proximal end 3 of the barrel 2 and a surface 12 which is substantially perpendicular to the inner wall 9 and which faces the distal end.

Advantageously, as shown, the inner wall 9 is provided with two further such projections 10a nearer the proximal end 3 of the barrel 2.

The syringe plunger, which is generally indicated by the reference 13, comprises a stopper 14, a rod 15 and a gripping member 16. The stopper 14 has two integral annular sealing rings 17 and a distal end 18 having a shape which is complementary to that of the abutment surface 6 of the barrel against which the distal end 18 abuts at full advance of the plunger 13 in the barrel. The proximally facing surface 19 of the plunger stopper 15 is perpendicular to the direction of movement of the plunger 13 in the barrel.

The junction 20 between the stopper 14 and the rod 15 is of reduced diameter to be breakable for a purpose to be described. The barrel 2 and the plunger 13 are conveniently moulded of a plastic material with the needle 8 being moulded in the mounting 7.

Referring to FIG. 3, the inclined surfaces of the projections 10a together with a degree of resilience in the plunger stopper 14 enable the piston to slide over the projections and into the illustrated position between the two sets of projections 10a and 10. The assembled syringe may then be sold in a suitable sterilized packaging (not illustrated) and is removed from such packaging prior to use.

Figure 7:
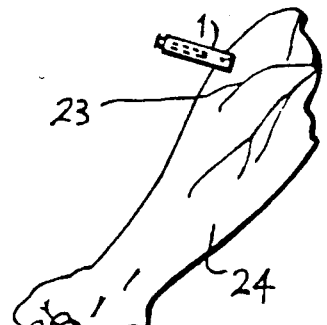

The operation of the syringe will now be described with reference to FIGS. 3 to 9. With the plunger stopper 14 in the position illustrated in FIG. 3, adjacent the ramp surfaces 11 of the projections 10, the needle 8 is pushed into a sachet 21 (FIG. 4) or bottle 22 (FIG. 5) of a liquid, e.g. a medicament, drug or medical solution and the plunger is withdrawn until the surface 19 of the stopper is adjacent or touches the surfaces 12 of the proximal projections 10a thus drawing the liquid into the syringe barrel 2. Any air remaining in the barrel is expelled in accordance with usual practice and the needle 8 is inserted into a person's body, in this case a vein 23, in the person's arm 24 (FIG. 7).

Figure 6:
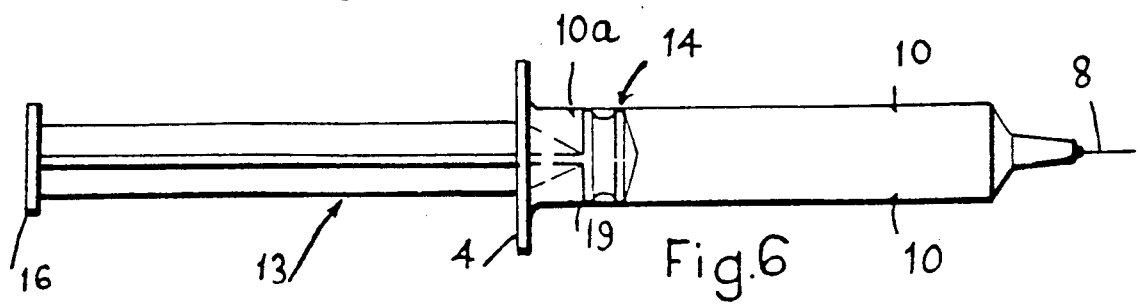

The syringe plunger 13 is then advanced, to discharge the liquid from the syringe 1 into the vein 23, from the position of the plunger piston 14 shown in FIG. 6 to that shown in FIG. 8 in which the distal end 18 of the stopper 14 abuts the distal end surface 6 of the barrel 2. During advance of the plunger 13 the stopper rides over the ramp surfaces 11 of the projections 10 and into the space between the perpendicular surfaces 12 of the projections 10 and the barrel end surface 6.

In order to reuse the syringe 1, it is, of course, necessary to retract the plunger 13 to recharge the syringe barrel with liquid. However, when this is done after advance of the plunger 13, the surface 19 of the stopper engages or abuts against the perpendicular surfaces of the projections 10 and the rod 15 breaks from the stopper 14 at the junction 20. Thus, the plunger minus the stopper is pulled out of the syringe barrel 2 and the stopper is left trapped between the surfaces 12 of the projections 10 and the distal end surface 6, leaving the syringe unfit for any further use as a syringe.

Referring now to FIGS. 10 to 14 of the drawings, there is shown another embodiment of a syringe which is generally indicated at 31 having a barrel 32 modulated of plastics material and comprising an integral distal nose 33 with a needle 34 moulded into the nose and projecting axially therefrom, and an integral proximal peripheral gripping member 35. The syringe also has a plunger 36 slidably mounted in the barrel 32 with its plunger rod 37 having a distal plunger stopper 38 which slidably and sealingly engages with the inner wall 39 of the barrel 32 and a proximal peripheral gripping member 40. The distal end region of the plunger rod 37 is provided with a stabilizing member 41 which diminishes wobble during advance and withdrawal movements of the plunger 36 in the barrel.

As is known the stopper 38 is provided with a standard end peg 42 over which a standard elastomeric cap 43 is frictionally fitted with its open end abutting against a disc 43a, with the maximum, advance injection stroke of the plunger being determined by abutment of the stopper 38 with a distal annular end stop 44. Except for the cap 43 the plunger 36 is moulded integrally of a plastics material.

For a purpose to be described the barrel has integral distal projection means located a predetermined distance from the end stop 44 and constituted by three circumferentially equispaced distal projections in the form of symmetrical circular in cross-section blips 45 extending from the inner wall 39 and similar integral proximal projection means located at a predetermined distance from the proximal end of the barrel and constituted by three circumferentially equispaced proximal projections in the form of symmetrical circular in cross-section blips 46 located intermediate, and equispaced from the blips 45 when viewed along the axis of the barrel 32.

The stopper 38 is integrally joined to the plunger rod 37 by resilient breakable means generally indicated at 48 and comprising outwardly extending wings 47. For clarity of understanding, reference will now be made to the enlarged views illustrated in FIGS. 24 to 27. Each wing 47 has an arcuate outer periphery as can be seen from FIG. 27 and is flexibly joined to the disc 43a of the stopper 38 and the piston rod 37 at two locations respectively with one radially outer location 49 being adjacent the barrel inner wall 39 where it is joined to the stopper and the other radially inner location 50 being adjacent the plunger axis where it is joined to axially extensions 37a of the plunger rod 37. Thus, the wings are effectively hinged at the two locations 49 and 50. The proximally facing surface of the disc 43a is provided with a central abutment or stop 51 to be engaged by the distally facing surface portions 52 of the wings 47 in axial alignment with the plunger rod extensions 37a and to delimit the amount of axial movement of the plunger rod 37 with respect to the stopper 38.

The principles of operation of the syringe 31 may be understood from FIGS. 28a to 28d to which reference will now be made. In FIG. 28a, the plunger 36 is being withdrawn in the direction of the arrow 53 from a position in which the wings 47 are disposed proximally of the blips 45, which initially causes extension of the resilient breakable means 48, enabled by bending the hinge locations 49 and 50 until the wings 47 are in positive placement with or engage with the barrel inner wall 39 as shown in FIG. 28a, whereupon the plunger becomes rigid, as it were, and it is only then that withdrawal of the plunger 36 becomes possible and the wings 47 slide smoothly along the barrel inner wall. Total withdrawal of the plunger 36 from the barrel 32 is prevented by the wings 47 engaging with the proximal blips 46 (see FIG. 12).

Referring to FIG. 28b in which the plunger 36 is being advanced in the direction of the arrow 54, the action of commencing the advance movement of the plunger causes compression of the resilient breakable means 48 enabled by bending at the hinge locations 49 and 50 until the wings 47 disengage the inner wall 39 and are prevented from any further radially inward movement by the engagement of the surface portions 52 of the wings with the abutment 51 whereupon the plunger becomes rigid, as it were, and can then be advanced in the barrel.

Thus, the plunger 36 can be simply and easily be advanced and withdrawn in the barrel between the blips 45 and 46 (see also FIGS. 11 and 12) to enable vein location to be carried out by the drug abuser and then charged with drug by moving the plunger in the direction of the arrow 53 in FIG. 28a until the wings 47 engage the proximal blips 46 (see FIG. 12) defining the end of the withdrawal stroke. Any air remaining in the syringe barrel is expelled and the located vein entered. Then the plunger 36 is pushed in the direction of the arrow 54 in FIG. 28a and fully advanced in the direction of the arrow head 55 in FIG. 28c. to the position of maximum injection during which time the wings 47 pass the distal blips 45 and the plunger stopper 38 abuts against the end stops 44 in the barrel 32 as illustrated in FIG. 13. So that none of the drug is wasted the drug abuser will want to flush the distal end region of the syringe barrel with blood, and indeed this is of vital importance and absolutely necessary to the drug abuser. If a once use only syringe does not enable "flush back", the drug abuser will go back to using the unsafe multiple use syringes.

The distance f (FIGS. 12 and 28c) between the distal blips 45 and the end stop 44 is such that it enables the drug abuser to enjoy adequate flushing of the distal end region of the syringe barrel with blood by moving the plunger stopper back and forth between the distal blips 45 and end stop 44 in the directions of the array heads 57 and 55 in FIG. 28c.

However, when the drug abuser pulls on the plunger 36 to withdraw the plunger into a position in which the syringe can be refilled with drug in the direction of the array 58 in FIG. 28d, the wings engage behind the blips 45 with increasing radially outward force as the resilient breakable means 48 is fully extended and can do nothing else but break at the hinge locations 50 to permanently detach the stopper 38 from the plunger rod 37 in the barrel 32 as shown in FIG. 28d and in FIG. 14 with the stopper 38 trapped between the blips 45 and the end stop 44. Breakage is much easier and infallible because in addition to breakable means 48 being subjected to an axial stress there is also a bending stress.

Since there is no limit to the drug abuser's ingenuity in making a syringe reusable if that is the only way he can immediately get a "fix", it is extremely important for a once only use syringe to be tamper-proof. The tamper-proof characteristics are incorporated in the resilient breakable means 48. Firstly the resilient breakable means 48 presents insufficient surface area for sticking the broken parts together and, in any event, none of the known adhesives are compatible with some of the plastics materials such as polypropylene, from which the syringe plunger could be made.

Secondly, if the distal end of the syringe barrel 32 were cut off e.g. along the imaginary dashed line 59 in FIG. 29, the stopper 38 withdrawn whilst it is still integral with the rod 37, the wings 47 filed down sufficiently to by-pass the distal blips 45, as shown in FIG. 29, and the distal barrel and glued back on, then withdrawal strokes of the plunger will be impossible since the wings will no longer engage the barrel wall and because of the resilience of the breakable means and the construction of the hinge locations 50, the breakable means will break at the hinge locations 50 before any withdrawal movement of the stopper 38 occurs.

FIG. 30 shows another embodiment, which differs from those previously described by having a proximal sprung arm 60 moulded integrally with the plunger rod 37 and engageable with the proximal end of the syringe barrel 32 to prevent inadvertent advance of the plunger 36 to trap the wings 47 behind the distal blips 45, but pushable in to permit normal advance of the plunger.

In the drawings comprising FIG. 31, the first embodiment as shown in FIGS. 1 to 9 is again illustrated to show one way of rendering the syringe needle 8 harmless after use to avoid contaminating others when disposed of e.g. in the garbage 61.

To this end the plunger is provided with a narrow axial bore 62 continuing into a wider proximal bore portion 63 opening onto the peripheral gripping member 16. By pushing the needle 8 into the bore 62 and engaging the end 7a of the nose 7 into the bore portion 63 in which it engages with a friction fit, the nose end 7a can be snapped off in the manner shown at 64 so that the needle is safely retained in the plunger and the two syringe parts can then be taken by the drug abuser 65 to a government needle exchange centre 66 to obtain a replacement syringe without any fear of contamination.

FIGS. 32 and 35 illustrate a syringe 70, in accordance with another embodiment of the present invention, which is particularly suitable for immunisation purposes, as it is capable of measuring and injecting precise quantities of vaccine, which are usually small, e.g. 0.5 ml.

The syringe 70 includes a syringe barrel 71 having a gripper member 72 at its proximal end and a none 73a for retaining a syringe needle (not shown) at its distal end. Projection means in the form of a plurality of rings 73 extend from the inner wall of the barrel 71 and are each precisely located relative to the distal end of the barrel, such that the first ring nearest the distal end measures accurately a 0.5 ml. quantity of liquid, usually a vaccine, to be injected and the successive three rings each measure a predetermined additional quantity in excess of 0.5 ml.

A syringe plunger initially consists in two parts 74a and 74b. Plunger part 74a has a gripping member 75 at its proximal end and a plunger rod part 76, which has two longitudinal parallel grooves 77 formed in opposite sides thereof and extending from the distal end 78 of plunger part 74a to an abutment surface 79a. The distal end 78 of the rod part 76 is integrally joined by resilient breakable means constituted by a breakable joint 79, shown in FIG. 35 to two rings 80. The other plunger part 74b consists in a rod part 81 having a stopper 82 at its distal end and being formed with a longitudinal slot 83 ending in a pair of hooks 84.

The two plunger parts are assembled by sliding the hooks 84 into the grooves 77 respectively via the distal end 78, such that the central portion of the rod part 76 along its longitudinal axis and between the grooves 77, engages in the slot 83. The assembled plunger is inserted into the barrel 71, such that the stopper 82 sealingly engages with the inner wall of the barrel 71 on the distal side of the rings 73, and the wings 80 are located on the proximal side of the rings 73, as shown in FIG. 33.

The plunger is withdrawn to enable vaccine 85 to be drawn into the barrel 71 to a level corresponding to, for example the first of the rings 73 by the hooks 84 engaging with the distal end 78 of the plunger rod part 76. The plunger part 74a is then advanced so that the hooks 84 slide within the grooves 77, thus forming a lost motion mechanism, until they abut against the abutment surfaces 79. Continued advance of the plunger part 74a then also advances the plunger part 74b, so that the stopper 82 is pushed to the distal end of the barrel 71 and the vaccine 85 is injected. This continued advanced also pushes the wings 80 down the barrel 71 past the rings 73 to the full extent within the slot 83, as shown in FIG. 34.

Subsequent withdrawal of the plunger causes the wings 80 to engage with the first ring 73 and the breakable joint 79 thus breaks and the rod part 76 becomes permanently detached from the rod part 81 and thus the stopper 82, which is retained in the end of the barrel 71. In this way, the syringe is rendered useless after a single injection.

The lost motion effect of this syringe thus enables the stopper to be initially withdrawn within the barrel to draw vaccine into the barrel to a level corresponding to any one of the four rings 73 without causing premature engagement of the wings 80 with any of the rings and thus premature breakage of the breakable joint 79, and also prevents any further withdrawal without breaking after the wings have passed the most proximal ring.

Whilst particular embodiments have been described, it should be appreciated that the invention is not limited thereto but includes all modifications and variations falling within its scope. For example the plunger stopper 38 of the embodiment of FIGS. 10 to 28 could be like that of the syringe illustrated in FIG. 31 and vice-versa. And, of course, the plunger rod 37 of the embodiment of FIGS. 10 to 28 could be provided with needle disabling means like that shown in FIG. 31.

I claim:

1. A one use only syringe comprising a barrel and a plunger in slidable and sealing engagement with the inner wall of the barrel, the barrel having projection means and the plunge having breakable means, characterized in that the projection means project from an inner wall of the barrel and into a path of movement of the plunger stopper and in that the breakable means is integral in a one-piece portion of the plunger and constitutes a breakable connection in the one-piece portion between at least one part of the plunger rod and the plunger stopper the arrangement being such that during either one of advance and withdrawl of the plunger, engagement of the plunger with the projection means causes the breakable connection to break and thus the plunger stopper to break away from the said at least one part of the plunger rod.

2. A syringe as claimed in claim 1, wherein the plunger (13; 36; 74a, 74b) is arranged to engage with the projection means (10; 45; 73) during withdrawal of the plunger (13; 36; 74a, 74b) following a full advance injection stroke.

3. A syringe as claimed in claim 2, wherein said projection means (10; 45; 73) is located at such a distance from the distal end of the barrel (2; 32) to permit flushing movements of the plunger stopper (14; 38) prior to the breakable means (20; 48) being broken upon subsequent withdrawal of the plunger (13; 36).

4. A syringe as claimed in claim 2, wherein the projection means (10; 45) is arranged such that the plunger stopper (14; 38) can slide over it during advance of the plunger (13; 36) to discharge a liquid therefrom, yet cannot move beyond the projection means (10; 45) during withdrawal so that any further withdrawal after the stopper (14; 38) has engaged with the projection means (10; 45) causes the stopper (14; 38) to break away from the plunger rod (15; 37).

5. A syringe as claimed in claim 4, wherein the breakable means (20; 48) consists of an integral breakable junction (20), provided between the plunger stopper (14) and the plunger rod (15), which is made weaker than the plunger rod (15) and stopper (14), and fracture or breakage of the junction (20) occurs due to axial stress induced therein when the plunger (13) engages the projection means (10) during withdrawal of the plunger (13) after a maximum injection stroke.

6. A syringe as claimed in claim 2, wherein the breakable means (20; 48) is resilient and moves radially outwards to engage with the inner wall of the barrel (32) during the withdrawal stroke of the plunger (36) and moves radially inwards to disengage the barrel inner wall during the advance stroke of the plunger (36) such that the breakable means (48) moves radially past the projection means (45) during maximum advance of the plunger (36) to inject a liquid from the syringe barrel (32) but engages with the projection means (45) during an attempt at a full withdrawal stroke following a maximum advance injection stroke, whereby to cause breakage of the resilient breakable means (48) and permanent detachment of the plunger rod (3) from the plunger stopper (38) as the withdrawal stroke is continued.

7. A syringe as claimed in claim 2 wherein the breakable means (20; 48) is resilient and moves radially outwards to engage with the inner wall of the barrel (32) during the withdrawal stroke of the plunger (36) and moves radially inwards to disengage the barrel inner wall during the advance stroke of the plunger (36) such that the breakable means (48) moves radially past the projection means (45) during maximum advance of the plunger (36) to inject a liquid from the syringe barrel (32) but engages with the projection means (45) during an attempt at a full withdrawal stroke following a maximum advance injection stroke, whereby to cause breakage of the resilient breakable means (48) and permanent detachment of the plunger rod (37) from the plunger stopper (38) as the withdrawal stroke is continued.

8. A syringe as claimed in claim 1 wherein another projection means (10a; 46) is provided nearer the proximal end (3) of the barrel (2; 32) in order to prevent total withdrawal of the plunger (13; 36) from the barrel (2; 32) once the plunger (13; 36) has been inserted.

9. A syringe as claimed in claim 1 wherein the distal projection means (10; 45) comprises three distal projections which are of arcuate form and which are equispaced around the inner circumference of the barrel (2; 32).

10. A syringe as claimed in claim 1 wherein said proximal projection means (10a; 46) comprises three projections which are equispaced around the inner circumference of the barrel (2; 32), such that they occupy positions which are intermediate, and are equispaced from, the distal projections.

11. A syringe as claimed in claim 1, wherein the projection means (10; 45; 73) is in annular form extending around the inner circumference of the barrel (2; 32; 71).

12. A syringe as claimed in claim 1, wherein the plunger comprises two parts (74a, 74b) which are slidably interconnected to form a lost motion mechanism with the breakable means (79) being integral with one (74a) of said parts and the other part (74b) including the plunger stopper (82).

13. A syringe as claimed in claim 12, wherein the said projection means (10; 45; 73) comprises a plurality of rings (73) each extending around the inner circumference of the barrel (71) at respective predetermined distances from the distal end of the barrel (71).

14. A syringe as claimed in claim 12, wherein said one part (74a) is formed with two longitudinal grooves (77) and the other part (74b) is formed with hooks (84) which are respectively slidably movable within said grooves (77).

15. A syringe as claimed in claim 1, including advance prevention means (60) located in the proximal end of the plunger rod (37) and, in a normal position, cause interengagement between the plunger rod (37) and the syringe barrel (32) to prevent unwanted advance of the plunger (36) in the barrel (32).

16. A syringe as claimed in claim 15, wherein the advance prevention means (60) consists in a sprung arm (60) moulded integrally with the distal end region of the plunger rod (37) which in its normal position engages with the distal end of the barrel (32) but can be pushed in to allow a full advance stroke of the plunger (35) to take place.

17. A syringe as claimed in claim 1, wherein the syringe is formed from two moulded parts, one part being the barrel (2; 32) with the needle (8; 34) of the syringe moulded therewith and the other part being the plunger (13; 36).

18. A syringe as claimed in claim 17, wherein the plunger (13; 36) is formed from a one-piece plastics moulding consisting of a peg (42) over which an elastomeric cap (43) is fitted to engage with the inner wall of the barrel (2; 32).

19. A syringe as claimed in claim 1, wherein the plunger (13; 38) is provided with an axial bore (62), into which the needle (8; 34) is intended to be inserted and snapped off from the barrel (2; 32) after use of the syringe, so that the needle (8; 34) is safely retained in the plunger (13; 36).

20. A syringe comprising a barrel and a plunger in slidable and sealing engagement with an inner wall of the barrel, the barrel having projection means and the plunger having a rod, stopper and breakable means, characterized in that the projection means project from the inner wall of the barrel and into a path of movement of the plunger stopper and in that the breakable means is integral with at least a part of the plunger rod and constitutes a breakable connection between said at least one part of the plunger rod and the plunger stopper, the arrangement being such that during either one of advance and withdrawal of the plunger, engagement of the plunger with the projection means causes the breakable connection to break and thus the plunger stopper to break away from said at least one part of the plunger rod, the plunger being arranged to engage with the stopper means during withdrawal of the plunger following a full advance injection stroke of the plunger, the breakable means being resilient and moving radially outwardly to engage with the inner wall of the barrel during a withdrawal stroke of the plunger and moving radially inwardly to disengage the barrel inner wall during the advance injection stroke of the plunger such that the breakable means moves readily past the projection means during maximum advance of the plunger to inject a liquid from the barrel and engages with the projection means during an attempt at a full withdrawal stroke following a maximum advance injection stroke so as to cause breakage of the resilient breakable means and permanent detachment of the plunger rod from the plunger stopper as a withdrawal stroke is continued, an outer periphery of the resilient breakable means comprising at least two wings which are engageable and disengageable, respectively, from the inner wall of the barrel during the withdrawl stroke and advance stroke with resilience being provided by the wings, each wing being flexibly joined to the stopper at a radially outer location adjacent the barrel inner wall and at a radially inner location adjacent a central axis of the plunger.

* * * * *